(12) United States Patent
Ueno et al.

(10) Patent No.: US 10,605,928 B2
(45) Date of Patent: Mar. 31, 2020

(54) DOSIMETER AND RADIOTHERAPY SYSTEM

(71) Applicant: HITACHI, LTD., Tokyo (JP)

(72) Inventors: Yuichiro Ueno, Tokyo (JP); Takahiro Tadokoro, Tokyo (JP); Yasushi Nagumo, Tokyo (JP); Shuichi Hatakeyama, Tokyo (JP); Kouichi Okada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/063,707

(22) PCT Filed: Mar. 16, 2016

(86) PCT No.: PCT/JP2016/058229
§ 371 (c)(1),
(2) Date: Jun. 19, 2018

(87) PCT Pub. No.: WO2017/158743
PCT Pub. Date: Sep. 21, 2017

(65) Prior Publication Data
US 2019/0018148 A1   Jan. 17, 2019

(51) Int. Cl.
*G01T 1/02* (2006.01)
*G01T 1/20* (2006.01)
(Continued)

(52) U.S. Cl.
CPC ............... *G01T 1/023* (2013.01); *A61N 5/10* (2013.01); *A61N 5/1071* (2013.01); *G01T 1/026* (2013.01);
(Continued)

(58) Field of Classification Search
CPC ........ A61N 5/10; A61N 5/1071; G01T 1/023; G01T 1/026; G01T 1/161; G01T 1/20; G01T 1/36
See application file for complete search history.

(56) References Cited

U.S. PATENT DOCUMENTS 5,331,961 A * 7/1994 Inaba ................. A61B 6/4057
250/367
5,434,415 A * 7/1995 Terada ..................... G01T 1/20
250/367
(Continued)

FOREIGN PATENT DOCUMENTS

JP   10-213663 A   8/1998
JP   2001-208850 A   8/2001
(Continued)

OTHER PUBLICATIONS

International Search Report of PCT/JP2016/058229 dated May 24, 2016.
(Continued)

*Primary Examiner* — Marcus H Taningco
(74) *Attorney, Agent, or Firm* — Mattingly & Malur, PC

(57) ABSTRACT

The dose measurement device includes: a radiation sensor constituted by a light emitting portion that is made of a polycrystalline scintillator and emits light of intensity dependent on an amount of incident radiation and a cover covering the light emitting portion; an optical fiber that is connected to the radiation sensor and transmits the photons emitted by the polycrystalline scintillator; a photoelectric converter for converting the photons transmitted by the optical fiber into electrical signals; a calculation device for measuring each of the electrical signals through the conversion by the photoelectric converter of each photon, calculating a count rate, and specifying a dose rate; and a display (Continued)

device for displaying measurement results calculated by the calculation device.

10 Claims, 5 Drawing Sheets

(51) Int. Cl.
*G01T 1/29* (2006.01)
*A61N 5/10* (2006.01)
*G01T 1/161* (2006.01)
*G01T 1/36* (2006.01)

(52) U.S. Cl.
CPC ............... G01T 1/20 (2013.01); G01T 1/29 (2013.01); *G01T 1/161* (2013.01); *G01T 1/36* (2013.01)

(56) References Cited

U.S. PATENT DOCUMENTS

| | | | |
|---|---|---|---|
| 5,905,262 A * | 5/1999 | Spanswick | G01T 1/161 250/361 R |
| 6,563,120 B1 * | 5/2003 | Baldwin | G01T 1/203 250/361 R |
| 2002/0001068 A1 * | 1/2002 | Iwanczyk | A61B 6/4057 353/121 |
| 2003/0168602 A1 * | 9/2003 | Testardi | A61N 5/1048 250/363.01 |
| 2008/0128623 A1 | 6/2008 | Srivastava | |
| 2009/0014665 A1 | 1/2009 | Fleming et al. | |
| 2013/0114798 A1 * | 5/2013 | Hintenlang | A61B 6/00 378/205 |
| 2013/0304409 A1 * | 11/2013 | Beaulieu | G01T 7/005 702/104 |
| 2014/0225094 A1 * | 8/2014 | Fraboni | H01L 51/0003 257/40 |
| 2014/0252238 A1 * | 9/2014 | Jung | G01T 1/023 250/362 |
| 2016/0103227 A1 * | 4/2016 | Beddar | G01T 1/29 250/252.1 |
| 2018/0321389 A1 * | 11/2018 | Jung | G01T 1/023 |

FOREIGN PATENT DOCUMENTS

| | | | |
|---|---|---|---|
| JP | 2007-139435 A | | 6/2007 |
| JP | 2008-138199 A | | 6/2008 |
| JP | 2009-36752 A | | 2/2009 |
| JP | 2009-524835 A | | 7/2009 |
| JP | 6345471 B2 | * | 6/2018 |
| KR | 20090119033 A | * | 11/2009 |
| WO | 2010/017218 A2 | | 2/2010 |
| WO | 2014/012141 A1 | | 1/2014 |

OTHER PUBLICATIONS

English translation of Korean Publication No. 2009-0119033 published Nov. 19, 2009.
Extended European Search Report received in corresponding European Application No. 16894361.1 dated Oct. 16, 2019.

* cited by examiner

[FIG. 1]
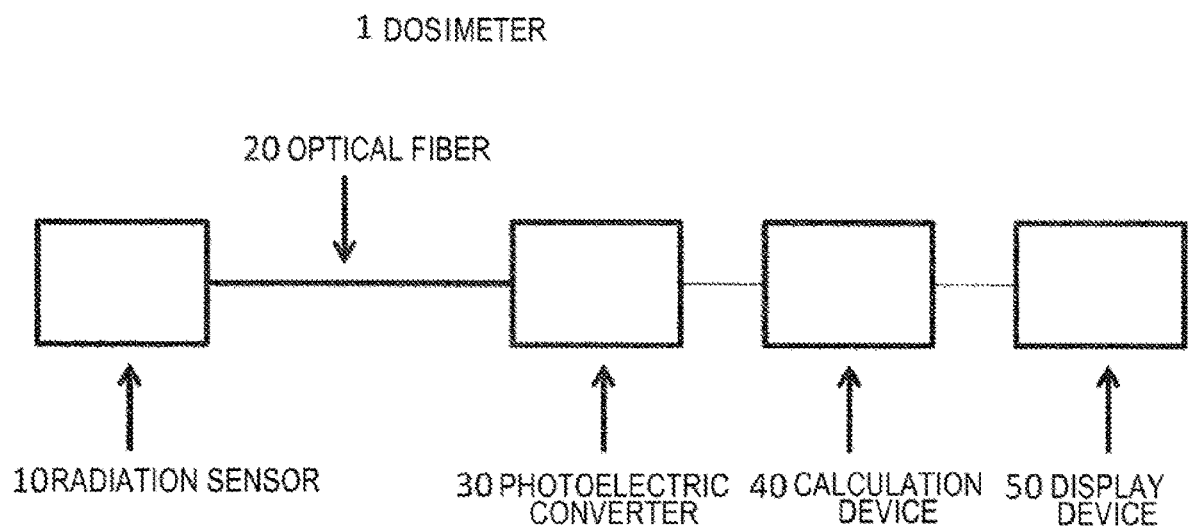
[FIG. 2]
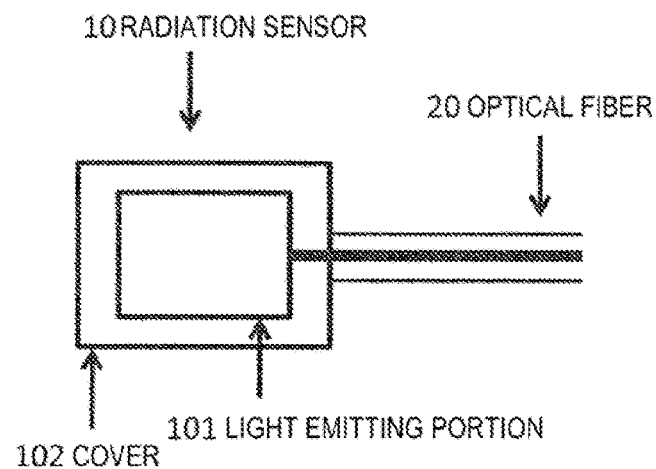

[FIG. 3]
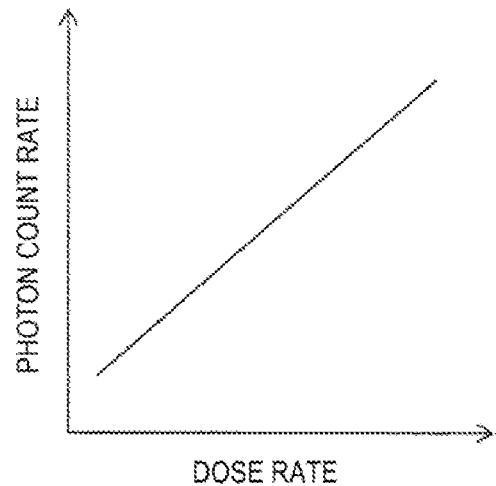
[FIG. 4]
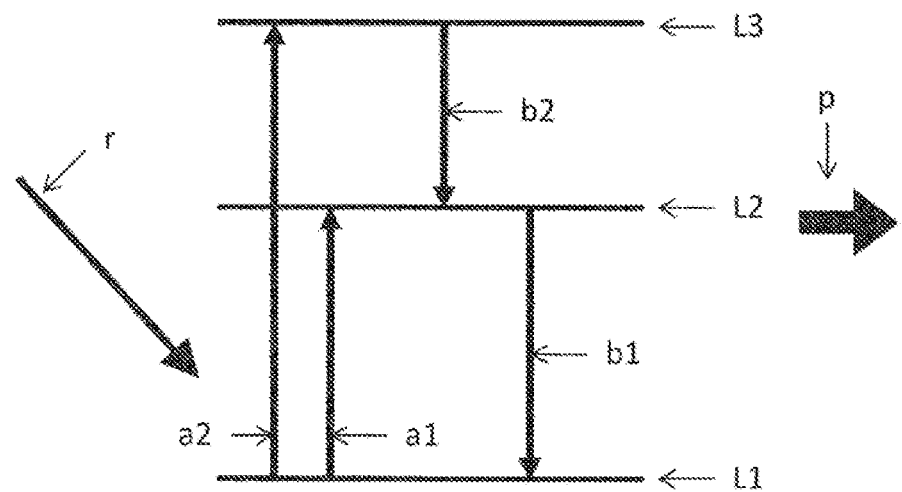

[FIG. 5]
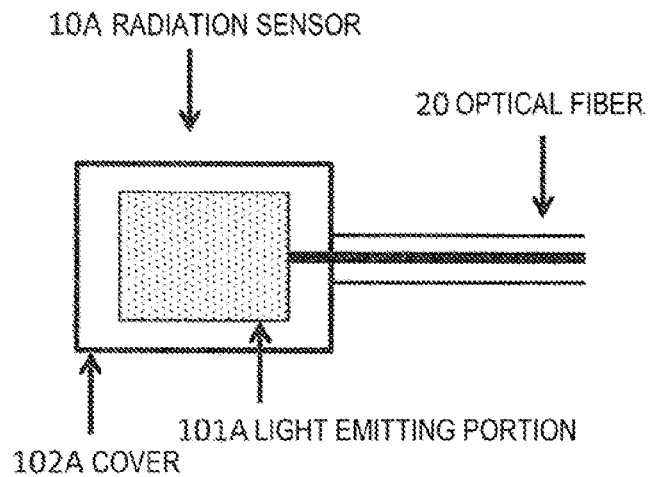
[FIG. 6]
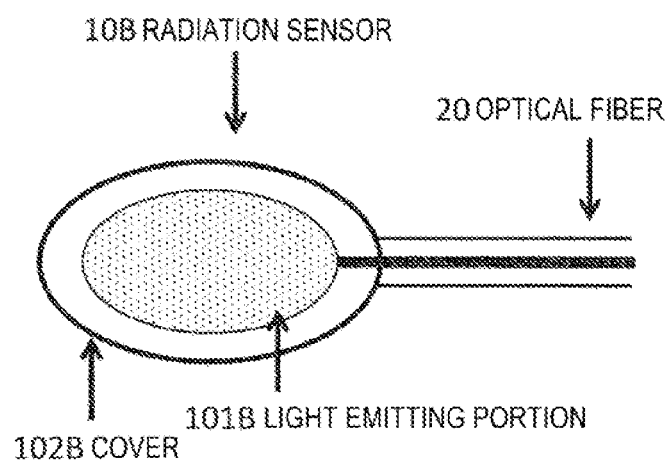

[FIG. 7]
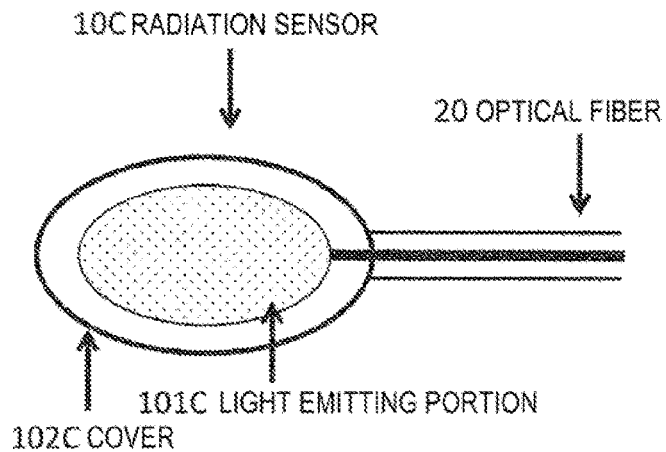
[FIG. 8]
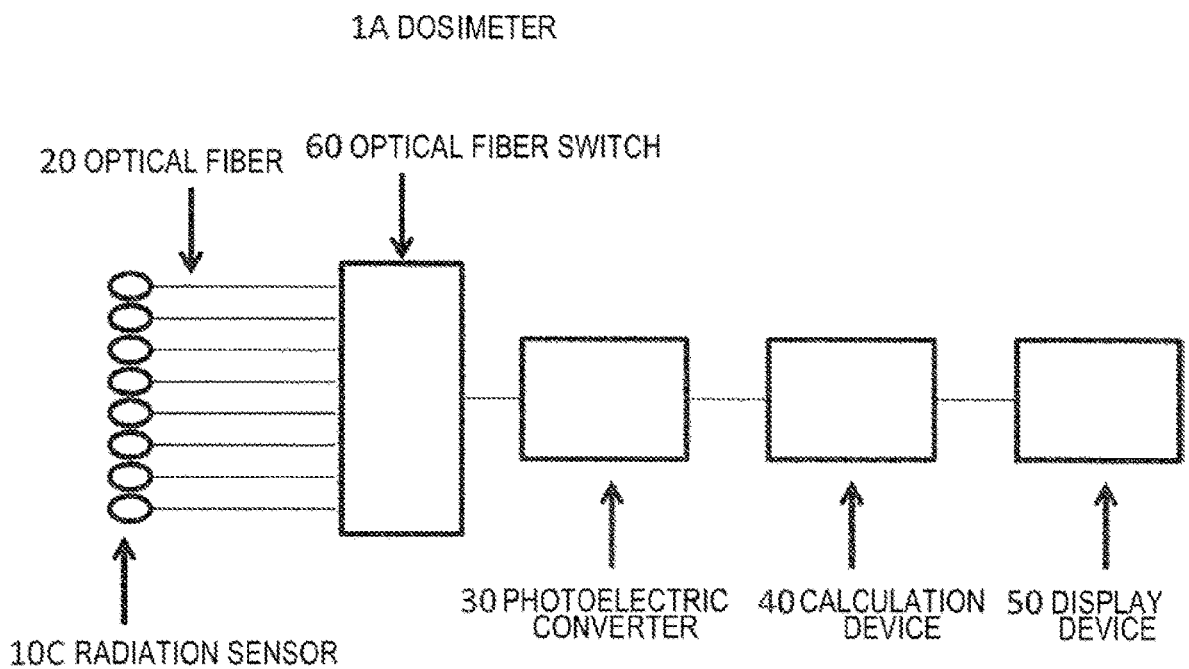

[FIG. 9]
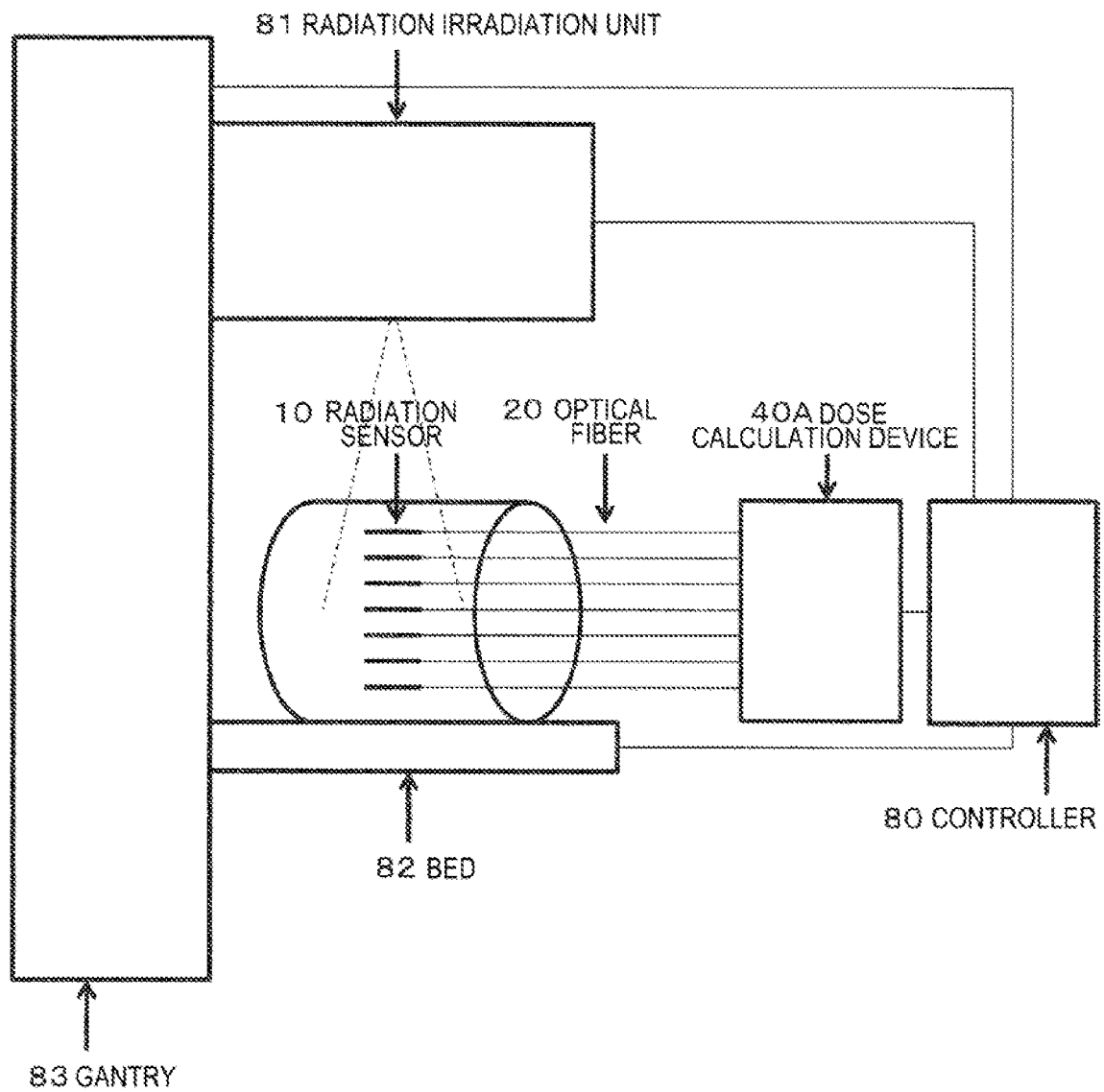

DOSIMETER AND RADIOTHERAPY SYSTEM

TECHNICAL FIELD

The present invention relates to a dosimeter and a radiotherapy system.

BACKGROUND ART

The first cause of death in Japan is cancer and is steadily increasing, and radiation cancer treatment has attracted attention as a therapy method in Japan where improvement of the quality of life (QOL) is required in recent years. In order to improve the QOL as needs, radiation cancer treatment is beginning to spread widely in Japan, along with high precision of radiation cancer treatment which is a seed.

Radiation used for the treatment includes X-Rays, electron beams, proton beams, heavy particle beams, and neutron beams, but development of proton beam and heavy particle beam therapy systems has been particularly remarkable in recent years. Since the proton beams and the heavy particle beams can apply a dose concentrating on a tumor volume using properties that the energy is intensively deposited immediately before stopping to make a peak (black peak) of the dose, high-precision treatment with a minimal invasion can be expected. In the X-ray treatment, IMRT, IGRT, and the like have also been developed, and efforts to concentrate the dose rate on the tumor volume are progressing. As the radiotherapy system becomes more upgrading, it is required to improve precision of treatment planning, precision of patient positioning, and the overall precision related to radiation treatment up to the treatment planning and the measurement of the dose rate for QA of the system.

For the measurement of the dose rate in the radiation treatment, ionization chambers with good stability and reproducibility are widely used. The ionization chamber has limitation in downsizing due to its detection principle, and accordingly dose distribution measurement is performed using a semiconductor detector, which is relatively easy to downsize, instead of the ionization chamber. However, the semiconductor detector also has limitation in downsizing if a signal processing system is included. In addition, such a detector needs to apply a high voltage for measurement, and thus it is difficult to measure the dose rate by inserting into the body.

In addition, since such a detector has generally high-density and has large interaction with the radiation as compared with substances in the body or water, the influence of the detector itself cannot be ignored.

Therefore, as a detector capable of monitoring the dose rate in the body, a system having a scintillator and an optical fiber is effective, and the following techniques are known.

A radiation monitor disclosed in PTL 1 is characterized in that "using a scintillation fiber 2 emitting fluorescent light as a radiation detector, a combined one by fusion bonding to the scintillation fiber 2 and a light transmission fiber 3 for transmitting the fluorescent light which is made of a material same kind as this scintillation fiber 2 is connected to a light detector 4 changing the transmitted light to electrical pulse signal. The light emitted from the scintillation fiber 2 is detected by the light detector 4 of which signal is amplified with a preamplifier 5, measured with a measuring device 6 counting the electric pulse signal and this measured result is indicated with a display 7.", and is to exactly measure the absorbed dose near a cancer lesion by inserting a dose meter into the body.

In PTL 1, the scintillation fiber is used as a scintillator, but an elastic body is preferable in consideration of invasiveness at the time of inserting into the body. Further, the scintillator is preferably processed so as to correspond to various shapes in the body.

A radiation monitor disclosed in PTL 2 is characterized in that "the radiation monitor radiates fluorescence by accepting radiation, and the scintillation fiber 11 having flexibility is used for the detector part of the radiation. When the scintillation fiber 11 emits the fluorescence by receiving the radiation, the emitted fluorescent light is transmitted by the optical fiber 4 of the after stage to the photoelectric convertor 2 of the after stage, the light is converted into the electric signal by the photoelectric convertor 2, then inputted into the operation device 3 of after stage. In the operation device 3, the dosage rate of the radiation incident on the detection part is calculated from the electric signal, and displayed with its value of the dosage rate on the display device 10.", and is to measure the dose rate in a minute place using the scintillation fiber having flexibility.

In PTL 2, since the scintillation fiber having flexibility is used as the scintillator, the invasiveness at the time of inserting into the body is reduced. However, the scintillation fiber of PTL 2 does not have a wide dynamic range from low dose to high dose, so it has a problem that measurement accuracy is low.

CITATION LIST

Patent Literature

PTL 1: JP-A-10-213663
PTL 2: JP-A-2007-139435

SUMMARY OF INVENTION

Technical Problem

In order to measure a dose rate in the body, it is necessary to use a dosimeter which is compact and has a low degree of invasiveness as described above. Further, it is necessary to perform measurement with reproducibility in response to the shapes of organs, which are complicated and vary between individual organs, and changes in the shapes over time.

In addition, in the radiotherapy, it is significantly important to perform not only dose monitoring during treatment but also dose rate measuring for QA/QC such as measuring in the phantom. In various types of dose rate measurements for the radiotherapy, it is necessary to secure dose linearity in a wide dynamic range from low dose to high dose.

Further, as the treatment accuracy improves, more accurate measurement is required with higher spatial resolution. In order to meet this need, it is important to miniaturize the detector, and since the interaction with the radiation of the detector itself is also a problem, it is important that the material of the detector is also equivalent to the object to be measured (human body or phantom).

From the above, an object of the present invention is to provide a dosimeter that is small, has a low degree of invasiveness, and includes a sensor portion in response to the shapes of organs, which are complicated and vary between individual organs, and changes in the shapes over time, and a radiotherapy system.

Solution to Problem

In order to solve the problems described above, a dosimeter according to the present invention is characterized by including: a radiation sensor constituted by a light emitting portion that is made of a polycrystalline scintillator and emits light of intensity dependent on an amount of incident radiation and a cover covering the light emitting portion; an optical fiber that is connected to the radiation sensor and transmits the photons emitted by the polycrystalline scintillator; a photoelectric converter for converting the photons transmitted by the optical fiber into electrical signals; a calculation device for measuring each of the electrical signals through the conversion by the photoelectric converter of each photon, calculating a count rate, and specifying a dose rate; and a display device for displaying measurement results calculated by the calculation device.

Advantageous Effects of Invention

According to the invention, an object thereof is to provide a dosimeter that is small, has a low degree of invasiveness, and includes a sensor portion in response to the shapes of organs, which are complicated and vary between individual organs, and changes in the shapes over time, and a radiotherapy system.

BRIEF DESCRIPTION OF DRAWINGS

FIG. 1 is a diagram illustrating a configuration of a dosimeter according to an Embodiment 1.

FIG. 2 is a cross-sectional view illustrating a radiation sensor of the dosimeter according to the Embodiment 1.

FIG. 3 is a diagram illustrating a relationship between a dose rate and a photon count rate according to the Embodiment 1.

FIG. 4 is a conceptual diagram illustrating a process of generating photons (light) by radiation incident on a light emitting portion according to the Embodiment 1.

FIG. 5 is a cross-sectional view of a radiation sensor of the dosimeter according to an Embodiment 2.

FIG. 6 is a cross-sectional view of a radiation sensor of the dosimeter according to an Embodiment 3.

FIG. 7 is a cross-sectional view of a radiation sensor of the dosimeter according to an Embodiment 4.

FIG. 8 is a diagram illustrating a configuration of a dosimeter according to an Embodiment 5.

FIG. 9 is a diagram illustrating a configuration of a radiotherapy system according to an Embodiment 6.

DESCRIPTION OF EMBODIMENTS

The present invention relates to a dosimeter in which a scintillator is connected to an optical fiber, and each of photons emitted from the scintillator is measured to calculate a count rate, thereby obtaining a dose rate. Hereinafter, modes for carrying out the invention (referred to as "embodiments" below) will be described in detail with reference to the drawings as appropriate.

Embodiment 1

A dosimeter according to an Embodiment 1 will be described with reference to FIGS. 1 and 2.
<Dosimeter>

FIG. 1 is a diagram illustrating a configuration of a dosimeter 1 according to the Embodiment 1.

The dosimeter 1 includes a radiation sensor 10, an optical fiber 20, a photoelectric converter 30, a calculation device 40, and a display device 50.

FIG. 2 is a cross-sectional view illustrating the radiation sensor 10. The radiation sensor 10 has a shape of covering a light emitting portion 101 with a cover 102.

The light emitting portion 101 is made of a polycrystalline scintillator and emits light of intensity dependent on an amount of incident radiation. The scintillator contains at least one kind of rare earth elements. Specifically, the scintillator is composed of, for example, a material such as transparent yttrium aluminum garnet as a base material and rare earth elements such as ytterbium, neodymium, cerium and praseodymium contained in the base material.

Since the scintillator contains at least one kind of rare earth elements as described above, it is possible to improve the linearity between the dose rate of the radiation incident on the radiation sensor 10 and the intensity of light, so that the dosimeter 1 can further accurately measure the dose rate of the radiation even when radiation of a high dose rate is incident.

Since the light emitting portion 101 is made of a polycrystalline scintillator, it can be formed into an arbitrary shape as compared with a single crystal.

As described above, since processing into an arbitrary shape can be possible, it is possible to realize a shape optimum for measuring complicated organs. Further, it is possible to change the shape of the sensor individually in response to the shapes of organs and changes in the shapes over time, thereby greatly improving measurement accuracy and reproducibility. Further, since the material (shape, hardness, density, etc.) of the sensor portion can be controlled, it is possible to provide a dosimeter with a low degree of invasiveness.

The cover 102 may be made of a light-shielding material that transmits gamma rays to be measured but does not allow external light to enter. From the viewpoint of sensitivity, a material that reflects light emitted by the light emitting portion 101 may be used. As a specific example thereof, aluminum or the like can be used. In addition, if the cover is an elastic body, a low degree of invasiveness can be realized.

The optical fiber 20 is connected to the light emitting portion 101, and transmits the generated photon to the photoelectric converter 30 connected to the opposite side thereof. As for a material composing the optical fiber 20, quartz, plastic, and the like may be used, for example.

The photoelectric converter 30 is a converter which is connected to the optical fiber 20 to transmit one electrical pulse with respect to one photon of transmitted light. As an example of the photoelectric converter 30, a photomultiplier tube, an avalanche photodiode, or the like can be adopted. By using these photomultiplier tubes or the like, it is possible to convert light (photons) into electrical pulses in which currents are amplified.

The calculation device 40 is connected to the photoelectric converter 30, counts each of electrical pulses converted from each of photons by the photoelectric converter 30, and converts the count rate of the measured electrical pulses into a dose rate of radiation. Specifically, the calculation device 40 includes a storage device (not illustrated) that stores a data table in which the count rate of electric pulses is associated with the dose rate of radiation, and performs calculating process of converting the count rate of electric pulses into a dose rate of radiation by the data table. The calculation device 40 is not particularly limited as long as it can convert the count rate of electrical pulses into a dose rate of radiation, and for example, a personal computer having a function described above may be adopted.

The display device 50 displays the dose rate or the like calculated by the calculation device 40 and further can display abnormality or the like of the dosimeter 1.

The inventor experimentally found that there is a one-to-one correspondence relationship between the dose rate of the incident radiation and the number of photons per unit time (hereinafter also referred to as a "count rate of photons") emitted by the light emitting portion 101, as illustrated in FIG. 3. Incidentally, it is generally known that there is a one-to-one correspondence relationship between the count rate of photons and the count rate of electric pulses. Accordingly, since it is convinced that there is also a one-to-one correspondence relationship between the dose rate of radiation and the count rate of the electric pulse, by using this relationship, the count rate of the obtained electric pulse can be converted into the dose rate of radiation.

Here, the above-described correspondence relationship between the dose rate of the radiation and the count rate of the electrical pulse varies depending on the size, the shape, and the material of the light emitting portion 101 to be used, and the thickness and the length of the optical fiber 20. Therefore, the correspondence relationship is obtained in advance for each radiation monitor to prepare a data table, and thus it is possible to convert the count rate of the obtained electrical pulse into a dose rate of radiation. Further, what is derived using the calculation device 40 is not limited to the dose rate of radiation, and may be, for example, a temporal change of the dose rate.

Next, an operation of the dosimeter 1 will be described. FIG. 4 is a conceptual diagram illustrating a process of generating photons (light) by the incident radiation. When radiation r is incident on the light emitting portion 101 as illustrated in FIG. 4, by the energy of the radiation r, the rare earth atoms or the like in the light emitting portion 101 transit to an excited state (for example, the energy levels L2 and L3) of higher energy (see arrows a1 and a2 in FIG. 4).

On the other hand, when a rare earth atom or the like having high energy in the excited state (for example, the energy levels L2 and L3) transits (see arrows b1 and b2 in FIG. 4) to an excited state or a ground state (for example, energy levels L1 and L2) with lower energy, a photon p (photon) having energy corresponding to the energy difference is generated.

The photons p (light) generated as described above are transmitted to the photoelectric converter 30 via the optical fiber 20, and are converted into electrical pulses by the photoelectric converter 30. Next, the number of electrical pulses converted by the photoelectric converter 30 is counted by the calculation device 40, and the count rate of the obtained electric pulses is compared with the data table to convert into the dose rate of radiation, thereby obtaining the dose rate of the incident radiation.

As described above, the dosimeter includes the radiation sensor 10, the optical fiber 20, the photoelectric converter 30, the calculation device 40, and the display device 50 described above, it is possible to measure the incident radiation as a count rate of electrical pulses (count rate of photons), and thus a dose rate of the radiation can be measured easily and accurately. Further, the dosimeter has the above-described configuration, and does not feed high voltages, so that it is possible to reduce a risk of electric shock.

Embodiment 2

The dosimeter 1 of the present embodiment is characterized by a radiation sensor 10A, and the other configurations of the optical fiber 20, the photoelectric converter 30, the calculation device 40, and the display device 50 are the same as those of the Embodiment 1. The radiation sensor 10A will be described in detail with reference to FIG. 5.

It is characterized in the material of the radiation sensor 10A of the light emitting portion 101A. Specifically, the light emitting portion 101A is a mixture of a scintillator that emits light of intensity dependent on the amount of incident radiation and a light transmitting material that transmits the light emitted by the scintillator. The scintillator is the same as in the Embodiment 1 and contains at least one kind of rare earth elements. Accordingly, as in the Embodiment 1, it is possible to improve the linearity between the dose rate of radiation incident on the radiation sensor 10A and the intensity of light, and even when radiation of a high dose rate is incident on the dosimeter 1, it is possible to measure a dose rate of radiation with higher accuracy.

The light transmitting material may be any material that transmits light emitted by the scintillator, and may be made of resin or the like from the viewpoint of processability, for example. Specifically, plastic materials such as acrylic, polyethylene terephthalate, polycarbonate, polystyrene, and vinyl chloride may be included. Of course, it is not limited to these materials.

For molding the light emitting portion 101A, for example, a thermoplastic light transmitting material can be used. As the molding method, a method is used in which a powdery radiation light emitting material is melted in a light transmitting material heated to be a liquid state, and then cooling the resultant material to be cured. When curing, it may be poured into a mold that matches the shape of the examination site (organ etc.) and molded, or it may be cut into a required shape after curing. The molding method of the light emitting portion 101A is not limited thereto, and any method can be used as long as it is possible to mix the scintillator and the light transmitting material to mold it into an arbitrary shape.

Since the mixing amount of necessary scintillators can be adjusted, the count rate of photons can be adjusted. When the dose rate is low, by increasing the mixing ratio of the scintillators to increase the count rate, it is possible to shorten the measurement time or improve the measurement accuracy. When the dose rate is high, by lowering the mixing ratio of the scintillators, it is possible to prevent saturation of the circuit system and the like.

In addition, it is also possible to cope with a high dose field by using a light transmitting material with low permeability of photons, or by mixing materials that lower photon permeability.

The cover 102A may be a light-shielding material that transmits gamma rays to be measured but does not allow external light to enter and have a shape matching the shape of the light emitting portion 101A. From the viewpoint of sensitivity, a material that reflects light emitted by the light emitting portion 101 may be used. In addition, if the cover is an elastic body, a low degree of invasiveness can be realized.

By using a mixture of a scintillator and a light transmitting material for the light emitting portion 101A, processing into an arbitrary shape becomes easier, and a shape optimum for measuring complicated organs can be realized. Furthermore, it is possible to change the shape of the sensor individually in response to the variation of shapes of individual organs and changes in the shapes over time, thereby greatly improving measurement accuracy and reproducibility.

Embodiment 3

The dosimeter 1 of the present embodiment is characterized in that the radiation sensor 10B is made into an elastic body. Other configurations of the optical fiber 20, the photoelectric converter 30, the calculation device 40, and the display device 50 are the same as those in the Embodiment 1. The radiation sensor 10B will be described in detail with reference to FIG. 6.

The light emitting portion 101B is a mixture of a scintillator that emits light of intensity dependent on the amount of incident radiation and a light transmitting material that transmits light emitted by the scintillator and is an elastic material. The scintillator is the same as in the Embodiment 1 and contains at least one kind of rare earth elements. Accordingly, as in the Embodiments 1 and 2, it is possible to improve the linearity between the dose rate of radiation incident on the radiation sensor 10B and the intensity of light, and even when radiation of a high dose rate is incident on the dosimeter 1, it is possible to measure a dose rate of the radiation with higher accuracy.

The light transmitting material is a material that transmits light emitted by the scintillator and may be an elastic material. Specifically, polyvinyl chloride, styrene type TPE and the like may be used. Of course, it is not limited to these materials.

The light emitting portion 101B may be manufactured by a general rubber product manufacturing method for example, and may be subjected to molding to be formed into a desired shape by press molding, injection molding, or the like after manufacturing a raw material by kneading a powdery scintillator in the raw material. The molding method of the light emitting portion 101B is not limited thereto, and any method may be used as long as it is possible to mix the scintillator and the light transmitting material having elasticity to form into an arbitrary shape, and can adjust the mixing amount of the necessary scintillators.

The cover 102B may be made of a light-shielding material that transmits gamma rays to be measured but does not allow external light to enter, as long as it has elasticity similarly to the light emitting portion 101B.

By using a mixture of the scintillator and the light transmitting material having elasticity for the light emitting portion 101B, processing into an arbitrary shape becomes easier, and it is possible to realize a shape optimum for measuring complicated organs. Furthermore, it is possible to change the shape of the sensor individually in response to the variation of shapes of individual organs and changes in the shapes over time, thereby greatly improving measurement accuracy and reproducibility.

Furthermore, since the radiation sensor 10B (the light emitting portion 101B and the cover 102B) is an elastic body, the invasiveness can be greatly reduced when inserting into the body or the like. In addition, it can flexibly follow the deformation of organs in the body, and the measurement accuracy and reproducibility are improved.

Embodiment 4

The dosimeter 1 of the present embodiment is characterized in that the radiation sensor 10C is made equivalent to water. Other configurations of the optical fiber 20, the photoelectric converter 30, the calculation device 40, and the display device 50 are same as those in the Embodiment 1. The radiation sensor 10C will be described in detail with reference to FIG. 7.

The light emitting portion 101C is a mixture of a scintillator that emits light of intensity dependent on the amount of incident radiation and a light transmitting material that transmits light emitted by the scintillator. The scintillator is the same as in the Embodiment 1 and contains at least one kind of rare earth elements. Accordingly, as in the Embodiments 1 and 2, it is possible to improve the linearity between the dose rate of radiation incident on the radiation sensor 10C and the intensity of light, and even when radiation of a high dose rate is incident on the dosimeter 1, it is possible to measure a dose rate of the radiation with higher accuracy.

The light transmitting material is a material that transmits light emitted by the scintillator, and presence or absence of elasticity is not a problem. Specifically, there are examples of polyurethane resin, acrylic, silicone rubber and the like. Of course, it is not limited to these examples.

The light emitting portion 101C may be manufactured by a general rubber product manufacturing method as long as it is, for example, an elastic body, and may be subjected to molding to be formed into a desired shape by press molding, injection molding, or the like after manufacturing a raw material by kneading a powdery scintillator in the raw material. The molding method of the light emitting portion 101C is not limited thereto, and any method may be used as long as it is possible to mix the scintillator and the light transmitting material having elasticity and mold it into an arbitrary shape.

The cover 102C may be made of a light-shielding material that transmits gamma rays to be measured but does not allow external light to enter.

The characteristic is that the mixing ratio of the light transmitting material and the material of the cover 102C and the mixing ratio of the scintillator and the light transmitting material may be adjusted so that the radiation sensor 10C constituted by the light emitting portion 101C and the cover 102C becomes water equivalent. In addition, if necessary, a material that does not affect light propagation may be mixed in the optically transparent material to realize a composition equivalent to water.

Further, it is even better if the optical fiber 20 is also made of plastic which is close to water equivalent.

By using a mixture of the scintillator and the light transmitting material for the light emitting portion 101C, processing into an arbitrary shape becomes easier, and it is possible to realize a shape optimum for measuring complicated organs. Further, it is possible to change the shape of the sensor individually in response to the variation of shapes of individual organs and changes in the shapes over time, thereby greatly improving measurement accuracy and reproducibility.

Furthermore, when the radiation sensor 10C is equivalent to water, it becomes substantially equal to the internal organ, and even if the radiation sensor 10C is disposed near the organ irradiated with radiation during treatment, the influence on the dose distribution of radiation by the radiation sensor 10C can be ignored. Therefore, it is possible to monitor the dose rate during treatment with high accuracy.

When the dosimeter 1 is used in QC/QA of radiotherapy, since the radiation sensor 10C is equivalent to water, the influence of the radiation sensor 10C on the dose distribution of the radiation in the water phantom can be ignored. Therefore, measurement in water phantom can be made with high accuracy.

Embodiment 5

A dosimeter 1A of the present embodiment is characterized in that a plurality of sets of water equivalent radiation sensors 10C and optical fibers 20 to be connected thereto are provided, the radiation sensors 10C are disposed in a measurement target region, and dose rate distribution in the measurement target region is measured.

FIG. 8 is a diagram illustrating a configuration of the dosimeter 1A according to the present embodiment.

The dosimeter 1A is configured to include a plurality of sets of water equivalent radiation sensors 10C and optical fibers 20, an optical fiber switch 60, a photoelectric converter 30, a calculation device 40, and a display device 50.

The plurality of optical fibers 20 are connected to the photoelectric converter 30 via the optical fiber switch 60. The calculation device 40 also has a function of controlling the optical fiber switch 60 and the photoelectric converter 30, switches an optical fiber 20 to be connected, and successively converts the photon from the radiation sensor 10C into an electrical signal by the photoelectric converter 30.

In this embodiment, one optical fiber switch 60 and one photoelectric converter 30 are provided, but a plurality of optical fiber switches 60 and a plurality of photoelectric converters 30 may be used. In an extreme case, without the optical fiber switch 60, the photoelectric converter 30 may be connected to each of all the water equivalent radiation sensors 10C and the group of the optical fibers 20 respectively connected to the water equivalent sensors 10C, thereby performing measurement. The number of the radiation sensors 10C to be connected to the photoelectric converter 30 may be determined in consideration of a time relative to reading and the required sampling time.

Since a plurality of water equivalent radiation sensors 10C can be arranged in the measurement target region, it is possible to measure the dose distribution in the body or the water phantom with high accuracy without affecting radiation irradiation (dose distribution). Further, since the radiation sensor 10C is compact and can be disposed in plural, measurement can be performed with high spatial resolution.

Embodiment 6

The present embodiment describes a case where the dosimeter 1 described in the Embodiment 1 is incorporated in a radiotherapy system 100.

FIG. 9 is a diagram illustrating a configuration of the radiotherapy system 100 according to the present embodiment. The radiotherapy system 100 is configured to include a radiation sensor 10, an optical fiber 20, a dose calculation device 40A, a controller 80, a radiation irradiation unit 81, a bed 82, and a gantry 83.

The dose calculation device 40A has a function as the photoelectric converter 30 and the calculation device 40 of Embodiment 1, and specifically, is configured to include a photoelectric conversion unit, an amplifier, and a calculation unit.

The photoelectric conversion unit is similar to the photoelectric converter 30 of the Embodiment 1. The amplifier is connected to the photoelectric conversion unit, and amplifies and waveform shapes the electric pulse converted from the photon in the photoelectric conversion unit as necessary. The calculation unit is a device connected to the amplifier to count electric pulses amplified by the amplifier and convert the count rate of the measured electric pulse into the dose rate of radiation, and corresponds to the calculation device 40 of the Embodiment 1.

Based on the dose rate input from the dose calculation device 40A, the controller 80 controls the radiation irradiation unit 81 and the bed 82 installed in the gantry 83 so as to obtain the optimum absorbed dose distribution, and performs radiation irradiation. Specifically, the controller controls the dose rate by changing the intensity of radiation and the transmittance (energy such as X-rays or proton beams), changes the shape of the irradiation site by changing the collimator shape, or controls the irradiation point by changing the bed position. Of course, the controller is not limited to this, as long as it can control the absorbed dose rate distribution by exchanging a radiation filter, controlling an irradiation time, or the like.

Even if the dosimeters described in Embodiments 2 to 5 are incorporated in the radiotherapy system of this embodiment, it is possible to achieve the effects described in each of Embodiments 2 to 5.

REFERENCE SIGNS LIST

1: dosimeter
1A: dosimeter
10: radiation sensor
10A: radiation sensor
10B: radiation sensor
10C: radiation sensor
20: optical fiber
30: photoelectric converter
40: calculation device
50: display device
60: optical fiber switch
100: radiotherapy system
101: light emitting portion
101A: light emitting portion
101B: light emitting portion
101C: light emitting portion
102: cover
102A: cover
102B: cover
102C: cover

The invention claimed is:

1. A dosimeter comprising:
a radiation sensor constituted by a light emitting portion that is made of a polycrystalline scintillator and emits light of an intensity dependent on an amount of incident radiation and a cover covering the light emitting portion;
an optical fiber that is coupled to the radiation sensor and transmits photons emitted by the polycrystalline scintillator;
a photoelectric converter for converting the photons transmitted by the optical fiber into electrical pulse signals, wherein the photoelectric converter is configured to convert one photon into one electrical pulse signal;
a calculation device for counting the electrical pulse signals, calculating a count rate, and specifying a dose rate; and
a display device for displaying measurement results calculated by the calculation device.

2. A radiotherapy system comprising:
the dosimeter according to claim 1; and
a controller which controls a radiation irradiation unit and a bed based on a dose rate calculated by the dosimeter.

3. The dosimeter according to claim 1, wherein
a plurality of sets of the radiation sensors and the optical fibers connected to the radiation sensors are provided to measure a dose rate distribution.

4. The dosimeter according to claim 1,
wherein the polycrystalline scintillator includes a base material and at least one rare earth element.

5. The dosimeter according to claim 4,
wherein the base material is transparent yttrium aluminum garnet, and the rare earth element is at least one of ytterbium, neodymium, cerium and praseodymium.

6. The dosimeter according to claim 5,
wherein the rare earth element is neodymium.

7. A dosimeter comprising:
a radiation sensor constituted by a light emitting portion which is a mixture of a scintillator which emits light of an intensity dependent on an amount of incident radiation and a light transmitting material which transmits the light emitted by the scintillator, and a cover covering the light emitting portion;
an optical fiber that is connected to the radiation sensor and transmits photons emitted by the scintillator;
a photoelectric converter for converting the photons transmitted by the optical fiber into electrical pulse signals, wherein the photoelectric converter is configured to convert one photon into one electrical pulse signal;
a calculation device for counting the electrical pulse signals, calculating a count rate, and specifying a dose rate; and
a display device for displaying measurement results calculated by the calculation device.

8. The dosimeter according to claim 7, wherein
the radiation sensor is an elastic body.

9. The dosimeter according to claim 7, wherein
the radiation sensor is a water equivalent radiation sensor.

10. The dosimeter according to claim 9, wherein
a plurality of sets of the water equivalent radiation sensors and the optical fibers connected to the radiation sensors are provided to measure dose rate distribution.

* * * * *